US005531735A

United States Patent [19]
Thompson

[11] Patent Number: 5,531,735
[45] Date of Patent: Jul. 2, 1996

[54] MEDICAL DEVICES CONTAINING TRIGGERABLE DISINTEGRATION AGENTS

[75] Inventor: Samuel A. Thompson, Wilmington, Del.

[73] Assignee: Hercules Incorporated, Wilmington, Del.

[21] Appl. No.: 312,844

[22] Filed: Sep. 27, 1994

[51] Int. Cl.$^6$ .............................. A61K 9/22; A61K 9/14; A61F 2/00

[52] U.S. Cl. ...................... 604/891.1; 424/485; 424/486; 424/487; 424/48; 523/113; 523/115

[58] Field of Search .................................. 604/93, 891.1; 424/485, 486, 487, 488; 523/113, 115

[56] References Cited

U.S. PATENT DOCUMENTS

| | | | |
|---|---|---|---|
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,495,288 | 1/1985 | Jarvis | 435/241 |
| 4,902,295 | 2/1990 | Walthall | 623/11 |
| 4,923,645 | 5/1990 | Tsang | 264/4.2 |
| 4,938,763 | 7/1990 | Dunn et al. | 604/891.1 |
| 4,997,443 | 3/1991 | Walthall | 623/11 |
| 5,084,350 | 1/1992 | Chang | 428/402.4 |
| 5,160,745 | 11/1992 | DeLuca et al. | 424/487 |
| 5,324,519 | 6/1994 | Dunn et al. | 424/426 |

FOREIGN PATENT DOCUMENTS

| | | | |
|---|---|---|---|
| 0645150 | 3/1995 | European Pat. Off. | A61L 31/00 |
| 5229934 | 9/1993 | Japan . | |
| WO88/00237 | 1/1988 | WIPO . | |
| WOA8905671 | 6/1989 | WIPO | A61M 25/00 |

*Primary Examiner*—Paul R. Michl
*Assistant Examiner*—LaVonda R. DeWitt
*Attorney, Agent, or Firm*—Martin F. Sloan; Mark Goldberg

[57] ABSTRACT

The invention discloses temporary medical devices such as stent implants which can be disintegrated in-vivo upon demand by release of an agent held trapped within the device. The device is fabricated from a matrix polymer material which is essentially insoluble in body fluids and a disintegration agent which acts to initiate decomposition of the matrix polymer when contacted therewith. The disintegration agent is trapped within and chemically isolated from the matrix polymer such as by encapsulation, and is releasable within the matrix polymer upon contact of the device with a releasing agent which liberates the encapsulated disintegration agent.

37 Claims, No Drawings

MEDICAL DEVICES CONTAINING TRIGGERABLE DISINTEGRATION AGENTS

BACKGROUND OF THE INVENTION

FIELD OF THE INVENTION

The invention relates to medical devices, e.g., implants, which can be disintegrated in vivo upon demand by triggered release of an agent held trapped within the device.

DESCRIPTION OF RELATED ART

Medical devices are often used to facilitate the flow of material as, for example, in a ureteral stent used for drainage of urine from the kidney to the bladder, or in a vascular graft used to maintain blood flow.

Typically these medical devices have been made from durable, non-biodegradable materials such as metals, polyurethanes, polyacrylates, silicones etc. These non-biodegradable, non-dissolvable medical devices typically must be removed via an invasive procedure after they have served their purpose, or they remain in the body indefinitely. For those devices which remain in-vivo, there are often medical complications such as inflammation and other foreign body responses.

Devices have also more recently been prepared from biodegradable materials such as polyesters, polyanhydrides, and polyorthoesters. In U.S. Pat. No. 5,085,629, the use of a biodegradable polyester terpolymer of lactide, glycolide, and epsilon-caprolactone in a ureteral stent is disclosed. In the '629 patent, biodegradable has been defined to include hydrolytic instability. These polymers undergo hydrolytic chain cleavage in the presence of water to form low molecular weight water soluble species. The polyesters have been reported to undergo hydrolysis throughout the thickness of the device simultaneously (homogeneous hydrolysis) while the polyanhydrides and polyorthoesters have been reported to hydrolyse from the surface (heterogeneous hydrolysis).

There are several problems inherent to devices manufactured with these biodegradable materials. There is a significant loss of strength in the device prior to any significant weight loss. These devices may undergo failure into large pieces which may occlude the vessel in which they have been deployed. Biodegradable devices which undergo surface hydrolysis may eventually reach a thin skin configuration that may also lead to vessel occlusion. Semicrystalline biodegradable materials have also been shown to leave insoluble crystalline residuals in the body for very long periods of time.

Polysaccharide—metal salt systems have been used for many years in biomedical applications. In European Patent Application 0 507 604 A2, an ionically crosslinked carboxyl-containing polysaccharide is used in adhesion prevention following surgery. The ionically crosslinked polysaccharide is left in-vivo. No attempt to dissolve the material is made.

Hydrogels have been widely used in biomedical applications. In U.S. Pat. Nos. 4,941,870; 4,286,341 and 4,878,907, a hydrogel is used as a coating on an elastomer base in a vascular prosthesis. This hydrogel remains in-vivo. Kocavara et al in J. Biomed. Mater. Res. vol. 1, pp. 325–336 (1967) have reported using an anastomosis ureteral prosthesis prepared from a poly(hydroxyethyl methacrylate) hydrogel reinforced with polyester fibers. This prosthesis is designed to be left in vivo.

In U.S. Pat. No. 5,057,606, a method and article useful for preparing polysaccharide hydrogels is disclosed. These foamed and non-foamed gelled articles are prepared by mixing together a first component comprising a suspension of a water insoluble di- or tri-valent metal salt in an aqueous solution of a polysaccharide, with a second component comprising an aqueous solution of a water soluble acid optionally to include the water soluble polysaccharide. These gels remain in vivo.

It is also known in the art that biological agents, medicaments and cell tissue may be encapsulated within an ionically crosslinked structure or shell which is adapted to slowly release the capsule contents through permeation in vivo or ex vivo, or which are designed to quickly release the capsule contents in vivo or ex vivo by contact of the capsule with an agent which disrupts the ionically crosslinked capsule structure.

For example, in U.S. Pat. No. 4,407,957, an ionically crosslinked membrane gel is used to microencapsulate a core material. An interpolyelectrolyte complex is used to form a semipermeable membrane around the capsule. The membrane is reliquified through exposure to competing multi-valent ions followed by a treatment with a solution of competing poly-ionic polymer. Chelating agents such as citrate and ethylenediamine tetraacetic acid may be used to liquify the membrane gel. The core material is not released in vivo.

In JP 5,229,934(93), encapsulation of a medicated component dispersed in a hydrophilic hydrogel is disclosed. The capsule employed is covalently crosslinked and the core material is released by diffusion through the capsule. Release of core material is dependent upon time and cannot be triggered upon demand.

In U.S. Pat. No. 4,923,645, chelation and ion transfer are used to provide controlled release from gelled microcapsules. These microcapsules may optionally have an interpolyelectrolyte complex semipermeable membrane. Chelation and ion transfer are used to reversibly control release characteristics of the gelled microcapsule through modification of gel.

In U.S. Pat. Nos. 4,352,883 and 4,409,331, biological materials such as enzymes are encapsulated in semipermeable membranes which are prepared from interpolyelectrolyte complexes.

In PCT WO 8800237, cells or biological materials are encapsulated in a covalently crosslinked, permanent, semipermeable membrane.

In U.S. Pat. No. 5,084,350, capsules within capsules containing biological materials are prepared. The capsule membranes are semipermeable. The capsules are not contained within medical device nor are they used to release core material for disintegration of a medical device.

In U.S. Pat. Nos. 4,997,443 and 4,902,295, artificial transplant matrix tissue containing living cells is prepared by using a reversible gel material to manufacture a matrix over which a semipermeable membrane is prepared. After the semipermeable membrane has been made, the matrix is dissolved to leave living cells in a semipermeable membrane. The dissolution of the gel takes place ex vivo, and is not used to free the contents of the capsule.

In U.S. Pat. No. 4,495,288 a method of culturing anchorage dependant cells by encapsulation is disclosed. The cells can be harvested by exposing the capsule material to a chelating agent. The cells are not used to disintegrate a medical device and harvest is ex vivo.

The prior art discussed immediately above does not relate to the field of medical devices and does not disclose the in vivo disintegration of such devices via release of decomposition agents encapsulated within the device.

In U.S. application Ser. No. 08/128,952 filed Sep. 29, 1993, is disclosed medical devices prepared by treatment of ionically crosslinkable polymer compositions with crosslinking ion compositions to provide ionically crosslinked materials. These medical devices may then be disintegrated through the introduction into the body of a chemical trigger for such disintegration. This patent application does not describe the invivo disintegration of such devices via release of decomposition agents encapsulated within the device.

Accordingly, a primary object of the invention is to provide temporary medical devices such as implants which are essentially insoluble in and relatively inert with respect to normal body fluids, but which can be quickly disintegrated in-vivo by a chemical trigger mechanism controlled by the physician.

SUMMARY OF THE INVENTION

The present invention provides medical devices such as implants which can be structurally disintegrated or decomposed in vivo on demand by release of an agent trapped within the device, which agent is capable of initiating the decomposition of the device on contact into body fluid-soluble or dispersible components, e.g., water soluble or water dispersible components.

More particularly, the invention provides a medical device composition comprising a matrix polymer which is essentially insoluble or only very slowly soluble in body fluids such as water and a disintegration agent which acts to initiate decomposition of the matrix polymer when contacted therewith, the disintegration agent being contained within and chemically isolated from the matrix polymer and releasable within the matrix polymer upon contact of the composition with a releasing agent.

The disintegration agent may be chemically isolated from the matrix polymer by encapsulation in an ionically crosslinked second polymer or by chemically binding it as part of an interpolyelectrolyte complex within the matrix polymer. Contact of the composition with a releasing agent capable of displacing ions present in the ionically crosslinked second polymer or present in the interpolyelectrolyte structure will release the previously trapped disintegration agent for contact with the matrix polymer and lead to rapid decomposition of the medical device structure within the body.

The invention also provides shaped medical devices prepared from such compositions and processes for the in vivo decomposition of said devices.

DETAILED DESCRIPTION OF THE INVENTION

This invention provides medical devices which can be disintegrated upon demand by release of an agent held trapped within the device, said agent being capable of disintegrating the device. The agent is released by exposure of the device to an environment which acts to unencumber the agent. The agent is encapsulated or present as a component in an interpolyelectrolyte complex (IPEC) within the device. The releasing environment acts to weaken the capsule material or breakup the IPEC such that the disintegration agent is set free. Examples disintegration agents include but are not limited to enzymes, acids, bases, and electrolytes. Examples of releasing agents include but are not limited to aqueous acids, bases, electrolytes, and chelating agents. Examples of medical device matrix polymers which can be employed in this invention include natural polymers, synthetic polymers, and copolymers of natural and synthetic polymer units. The medical device composition is insoluble in normal body fluids in the absence of the disintegration agent releasing environment. The medical device comprises a polymeric material which may be covalently crosslinked, ionically crosslinked, non-crosslinked, linear or branched, glassy or semicrystalline.

The ionically crosslinkable polymers from which the matrix of the medical device may be fabricated may be anionic or cationic in nature and may include but are not limited to carboxylic, sulfate, and amine functionalized polymers such as polyacrylic acid, polymethacrylic acid, polyethylene amine, polysaccharides such as alginic acid, pectinic acid, carboxymethyl cellulose, hyaluronic acid, heparin, chitosan, carboxymethyl chitosan, carboxymethyl starch, carboxymethyl dextran, heparin sulfate, chondroitin sulfate, cationic guar, cationic starch, and their salts. Preferred ionically crosslinkable polymers are alginic acid, pectinic acid, carboxymethyl cellulose, hyaluronic acid, chitosan, and their salts. Most preferred ionically crosslinkable polymers are alginic acid, pectinic acid, and hyaluronic acid and their salts. Among the ionically crosslinkable cationic polymers that may be employed are chitosan, cationic guar, cationic starch and polyethylene amine.

The crosslinking ions may be anions or cations. Appropriate crosslinking ions include but are not limited to cations comprising an ion selected from the group consisting of calcium, magnesium, barium, strontium, boron, beryllium, aluminum, iron, copper, cobalt, lead, and silver ions. Anions may be selected from the group consisting of phosphate, citrate, borate, succinate, maleate, adipate and oxalate ions. More broadly the anions are derived from polybasic organic or inorganic acids. Preferred crosslinking cations are calcium, iron, and barium ions. The most preferred crosslinking cations are calcium and barium ions. The most preferred crosslinking anion is phosphate.

Other polymers from which the matrix of the medical device may be fabricated include non-crosslinked polymers which are subject to polymer chain degradation or accelerated hydrolysis when contacted with an enzyme or an acid or base. Examples of such polymers include polyesters such as polylactides, polyglycolides, polyhydroxy butyric acid, polyhydroxy valeric acid, polycaprolactone and their copolymers; polyanhydrides; polyorthoesters; poly-amino acids; polyvinylalcohol; polyoxymethylene and like materials. These materials may also be ionically or covalently crosslinked.

These polymers are selected such that they are essentially insoluble or only very slowly soluble in typical body fluids with which they will come in contact, e.g., urine, blood, bile, feces or intestinal fluids, but will become dispersed or dissolved in such fluids after contact with an appropriate disintegration agent as disclosed below.

The second polymeric material in which the disintegration agent is encapsulated or associated is an ionically crosslinkable polymer which may be the same as or different from the ionically crosslinkable matrix polymers described above from which the medical device itself is fabricated. Suitable materials include but are not limited to carboxylic, sulfate, and amine functionalized polymers such as polyacrylic acid, polymethacrylic acid, polyethylene amine, polysaccharides such as alginic acid, pectinic acid, carboxymethyl cellulose, hyaluronic acid, chitosan, carboxymethyl chitosan, carboxymethyl starch, carboxymethyl dextran, heparin sulfate, chondroitin sulfate, cationic guar, cationic starch, and their salts. Preferred ionically crosslinked capsule materials are alginic acid, pectinic acid, carboxymethyl cellulose, and chitosan and their salts. Most preferred ionically crosslinked capsule materials are alginic acid, pectinic acid, chitosan and their salts.

The capsule polymer is preferably a polyanionic polymer which is cationically crosslinkable with a polyvalent metal such as calcium, iron, aluminum or barium, most preferably calcium.

Agents which act to initiate decomposition of the matrix polymer present in the structured medical device when contacted therewith include but are not limited to enzymes such as amylase, pectinase, lysozyme, chitinase, proteolytic enzymes, esterases, and cellulases, acids such as lactic, glycolic, oxalic, formic, sulfuric, and phosphoric, bases such as the hydroxides and carbonates of magnesium, calcium, and aluminum; and electrolytes such as sodium, potassium, magnesium and lithium salts. An important feature of the invention is that these disintegration agents must be both at least partially water soluble and relatively inert and non-reactive with respect to the ionically crosslinked polymer in which they are encapsulated, since otherwise there would arise a premature triggering of the destruction of the capsule material and consequent decomposition of the medical device.

When it is desired to trigger the in-vivo release of the disintegration agent trapped within the matrix polymer forming the medical device, the device is contacted with a releasing agent which serves to displace (sequester or bind) the crosslinking ion present in the ionically crosslinked polymer forming the capsule wall. Releasing agents include organic acids and their salts or esters, phosphoric acid and salts or esters thereof, and sources of ions which can displace the crosslinking ion present in the capsule wall composition. Examples of releasing agents that displace a crosslinking ion include, but are not limited to ethylene diamine tetraacetic acid, ethylene diamine tetraacetate, citric acid and its salts, organic phosphates, such as cellulose phosphate, inorganic phosphates, as for example, pentasodium tripolyphosphate, mono and dibasic potassium phosphate, sodium pyrophosphate, and phosphoric acid, trisodium carboxymethyloxysuccinate, nitrilotriacetic acid, maleic acid, oxalate, polyacrylic acid, as well as sodium, potassium, calcium and magnesium ions. Preferred agents are citrate, inorganic phosphates, sodium, potassium and magnesium ions. The most preferred agents are inorganic phosphates and magnesium ions.

The matrix polymers forming the medical device are either porous materials or relatively non-porous materials. Water and other small molecules comprising the releasing agent will, in either case, be able to penetrate into the matrix polymer through various mechanisms, including diffusion. Capsule disruption will occur in those areas of penetration by the releasing agent, first at the surfaces of the matrix polymer. Matrix polymer degredation will then further occur, facilitating penetration of the releasing agent throughout the matrix polymer. Eventually, the entire article will be disrupted or disintegrated.

In one embodiment of this invention enzymes, chemical agents, or electrolytes are encapsulated in ionically crosslinked capsule compositions. These encapsulated agents are chosen for their ability to convert a medical device composition into water soluble species by cleavage of molecular bonds. The ionically crosslinked capsule compositions depend upon the presence of certain counterions to maintain a crosslinked state. Exposure of a medical device containing these encapsulated agents to an environment having displacing agents for the crosslinking counterions leads to a loss of integrity of the capsule and resultant release of the previously trapped disintegration agent (enzymes, chemical agents, or electrolytes). Released enzymes, chemical agents, or electrolytes act to convert the medical device to water soluble components.

For example, a medical device fabricated from a glutaraldehyde crosslinked thermoplastic starch containing calcium-alginate encapsulated amylase can be disintegrated and dissolved upon exposure to an environment that displaces calcium. This medical device composition will swell to some extent in body fluid. Swell is dictated primarily by the crosslink density. The device will be stable in this swollen state. Upon exposure of the device to a calcium binding agent such as inorganic phosphate, the capsule integrity will be disrupted and the amylase will be released, and the released amylase will hydrolyze the starch. The medical device will ultimately be reduced to water soluble components.

Encapsulation of a chemical agent which will convert the medical device into water soluble constituents is also within the scope of the invention. An example of this would be to entrap an acid which is capable of initiating or catalyzing cleavage of polymer chains forming the matrix polymer of the medical device.

One example of an ionically crosslinked medical device system is chitosan-borax, while one example of a non-crosslinked composition is chitosan. Each of these systems would contain an enzyme for chitosan (for example lysozyme or chitinase) encapsulated in an ionically crosslinked capsule such as calcium-pectate or calcium-alginate.

This invention can be applied to ionically crosslinked compositions which are sensitive to the disintegration trigger and also contain microencapsulated enzymes specific for degradation of the matrix polymer composition. An example of this would be a calcium pectate matrix composition which contains microencapsulated pectinase within calcium-alginate capsules. A suitable trigger such as inorganic phosphate would not only act to displace calcium crosslinking ions from the calcium-pectate matrix composition but would also displace calcium in the calcium-alginate capsules leading to release of pectinase and simultaneous degradation of the pectin chains enzymatically. This system would provide for amplification of the trigger as well as acceleration of disintegration of the calcium-pectate matrix composition.

In another embodiment of this invention, the disintegration agent may be present in the medical device in the form of an interpolyelectrolyte complex (IPEC). While a member in the IPEC, the disintegration agent is inactive against the medical device matrix composition. When the disintegration agent encounters an environment which favors ion displacement from the IPEC, the agent is released and becomes active in disintegration of the medical device. An example of an IPEC system can be found in the combination of an enzyme having an overall cationic charge such as lysozyme with a polyanionic polymer such as sodium alginate. The lysozyme, which is capable of disintegrating a medical device comprising chitosan, is inactive with respect to chitosan while complexed within the IPEC with sodium alginate. Upon exposure of the IPEC to an environment containing sufficient concentration of other cations (mono or poly), the lysozyme will be freed for activity against chitosan.

Disintegration of the medical devices of this invention is achieved through exposure of the ionically crosslinked composition which encapsulates or binds the disintegration agent, e.g., an enzyme, to agents which displace the crosslinking ion. Methods for introduction of the agent include: introduction through the diet of the patient, through parenteral feeding, introduction of a solution directly onto the device such as by insertion of a catheter which injects the agent within the device, or through an enema. The medical devices of the present invention are thereby removed as a consequence of the displacement of the ionic structure of the composition binding the disintegration agent and that agent's action on the matrix polymer forming the structure of the medical device. The disintegrated device is thereby removed safely from the body in the form of water soluble or water dispersible components.

For example, one technique for the disintegration of a urinary device such as an implanted ureteral stent decomposable by phosphate anions would be to include in the patent's diet materials which bind phosphate e.g., calcium salts, to lower the content of $PO_4^{3-}$ present in the urine which can be normally up to about 0.1%. When it is desired to remove the medical device, phosphate binders can be eliminated from the diet and also replaced by foods or substances which generate phosphate ions in the urine. Achievement of levels of phosphate in the urine of from 0.2 to 0.3% will result in the in-vivo decomposition of a chitosan stent containing a calcium alginate encapsulant and a lysozyme enzyme over a period of several days.

Medical devices which may be fabricated in accordance with this invention include stents, catheter or cannula components, plugs and constrictors, for both human and animal use. The invention is particularly applicable to medical stents of tubular configuration which come in contact with one or more body fluids such as blood, urine, gastrointestinal fluids, and bile. The devices are particularly applicable for use in gastrointestinal, urogenital, cardiovascular, lymphatic, otorhinolaryngological, optical, neurological, integument and muscular body systems.

The devices may optionally include water, fillers, other additives for medical treatment such as antiseptics, antibiotics, anticoagulants, or medicines, and additives for mechanical property adjustment of the device.

Linear device or pre-device configurations such as fibers, rods, tubes or ribbons can be manufactured in accordance with the present invention by using a spinning device in which a solution of an ionically crosslinkable matrix polymer is forced through a shaping die into a crosslinking bath containing the crosslinking ions. If the ionically crosslinkable polymer solution is aqueous, the product after crosslinking is typically described as a hydrogel. The hydrogel may be used as made or further given a three dimensional shape through treatment in a crosslinking solution after being forced into the desired shape. After equilibration, the hydrogel will retain the new three dimensional shape. The device may be used in its hydrogel form or in a dehydrated form. During dehydration the three dimensional shape is retained.

Another process for manufacturing the articles of the present invention comprises introducing a solution comprising ionically crosslinkable polymer through a die to form a tube, simultaneously pumping a solution comprising crosslinking ion through the formed tube, and extruding the formed tube from said die into a solution comprising crosslinking ion. In this process the crosslinking step may involve shaping of the device as in wet spinning of a tubular device. Alternatively, the device may be prepared by molding a latent crosslinking composition one or two part reaction injection molding system. The term "tubular" as used herein, includes not only cylindrical shaped devices having circular cross sections, but also devices having different cross sections as long as such articles have a hollow passageway which distinguishes a tube from a rod.

Another process for the manufacture of the devices of the present invention would be conventional molding techniques such as reaction injection molding wherein the ionically crosslinkable polymer and the crosslinking ion are mixed and introduced into a mold to form an article of the desired configuration.

In accordance with the present invention, the medical device may also be formed in-vivo. Such a method for medical treatment of humans and animals comprises introducing thereinto an ionically crosslinkable polymer and a crosslinking ion followed by crosslinking of said polymer to form a medical device selected from the group consisting of stents, catheter or cannula components, plugs, and constrictors, wherein said medical device comprises ionically crosslinked polymer.

More complex shaped devices can be made using a one or two part reaction injection molding composition. These molding compositions typically contain the ionically crosslinkable polymer in solution, the crosslinking ion in an insoluble or slowly soluble form and additives to cause dissolution of the crosslinking ion. When the crosslinking ion dissolves and dissociates, the ionically crosslinkable polymer solution gels. This gel (or hydrogel if the solvent is water) may be used as made or further developed, crosslinked and shaped by soaking in a solution of a crosslinking ion. Dissolution of the crosslinking ion to form the gel may be effected by using a two part molding system in which the second component contains an acid or pre-acid such as a cyclic lactone which lowers the pH and solubilizes the previously insoluble crosslinking ion.

Where the matrix polymer is non ionic, the device can be prepared by spinning or extruding a solution or melt of the polymer composition into a liquid bath and collecting the resultant shaped article.

Capsule manufacturing is accomplished by any of the microencapsulation techniques which are known in the art. Such techniques include but are not limited to: phase separation (simple or complex coacervation, salt coacervation), gelation (thermal, ionic), spray drying, centrifugal extrusion processes, air suspension coating, pan coating, emulsion hardening process, spray chilling, and rotational suspension separation.

The preferred embodiment of this invention is that where the capsule integrity is based upon ionic crosslinking of the capsule matrix. All of the processes listed above can be used to make capsules which may be ionically crosslinked as made, or ionically crosslinked after capsule manufacture.

One example of a process to make ionically crosslinked capsules is ionic gelation. Such a process includes: spraying an aqueous solution containing the core material (disintegration agent) and the capsule matrix polymer (anionic or cationic) into an aqueous solution of crosslinking ions (cations or anions). The core material will for the most part be trapped in the ionically crosslinked matrix. Untrapped core material can then be removed by washing.

An example of a process whereby a capsule is first made, then ionically crosslinked, is spray drying followed by treatment with crosslinking ions. The process is as follows: suspend particulated core material (disintegration agent) in a solution of capsule matrix polymer. Spray dry the suspension such that the capsule matrix polymer coats the core material and forms a dry coating. The dry capsules are then exposed to an aqueous solution of crosslinking ions to prepare the ionically crosslinked capsules.

Capsules can be mixed with the matrix polymer in many of the ways in which an inert filler would be mixed with the matrix polymer. Representative mixing techniques include but are not limited to suspension of the capsules in a matrix polymer solution, molten matrix polymer, matrix polymer monomer or prepolymer mixture, or powdered matrix polymer. If the encapsulated agent is thermally or environmentally sensitive, care must be taken in the selection of conditions which do not incapacitate the agent.

An IPEC may be formed simply by mixing the disintegration agent with the appropriately oppositely charged IPEC partner. Mixing of dilute solutions will lead to IPEC precipitation in the form of small discrete particles. The IPEC particles may be collected via filtration, spray drying, or simply further dissolving the matrix polymer directly in the IPEC suspension. When the IPEC is isolated, mixing with the matrix polymer can be done with solvent, thermally, or directly into matrix polymer monomer or prepolymer. Article fabrication by the methods described above will result in an IPEC filled article. If the matrix polymer is dissolved in the IPEC suspension, direct article formation via coagulation or crosslinking phenomenon can be achieved.

The medical devices of this invention are useful in medical applications where the removal of the standard non-disintegratable medical device involves patient discomfort and/or expense and in applications where a temporary device is therapeutically desirable. Examples of useful applications for these devices include ureteral, urethral, bilial, ileal and pyloric stents. In these applications, current state of the art stents must be removed by a second invasive procedure at great expense and patient discomfort. The devices of this invention facilitate removal, leading to reduced patient discomfort and expense. The medical devices of this invention are also useful in cardiovascular, lymphatic, neurological, integumental, skeletal, muscular, optical, otorhinolaryngological, oral, gastrointestinal and urogenital applications where controlled disintegration of the device is efficacious and in surgical procedures where a device is needed temporarily such as a cellular scaffold after which removal by dissolution is preferred. Other medical device applications may include adhesion prevention devices, drainage devices as in ear or sinus tubes, release devices in dental and medical applications, wound care as in the treatment of bed sores, temporary scaffold for bone, osteophilic coatings, neural growth guides, temporary stent for anastomosis, shaped delivery devices, hemostats, surgical sponges, hydrocephalus shunt, dialysis tubing, instrument coatings, patches for delivery systems, ostomy bags, form-fit wound care devices which are gelled on the patient, temporary plug, syringe deliverable temporary fill for aneurism repair, artificial skin, dental socket filler having therapeutic additives, temporary vena cava filter device, capsule for delivery of vena cava filter devices, deep vein thrombosis filter for orthopedic applications, dissolvable enteral feeding tube, enteral plugs, and hiatal hernia stents. Any of these devices may also act to release medicines, nutrients and the like.

The following examples are illustrative of the invention.

EXAMPLE 1

Encapsulation of lysozyme in ca-alginate fiber.

77.52 g of deionized water were weighed into a 4 oz glass jar. 2.40 g of sodium-alginate (Manugel DMB, Kelco) were added to the jar while mixing. After mixing for 1.5 hours, 0.080 grams of lysozyme (from chicken egg white, SIGMA Chemical Co.) were added to the sodium-alginate solution. Mixing was continued intermittently until all of the lysozyme had dissolved. The solution was transferred to a 10 cc syringe and extruded through a 0.5" long die having a 0.040" inside diameter into a 1% by weight solution of $CaCl_2 \cdot 2H_2O$ in deionized water to form a calcium-alginate fiber.

EXAMPLE 2

Preparation of chitosan tubing.

A 6% solution of chitosan (Fluka Chemical Co., medium molecular weight) was made in 6% citric acid in water. The chitosan solution was mixed at room temperature for 30 minutes followed by heating to 90° C. for 2 hours. The solution was then centrifuged to remove air. The solution was transferred to a 30 cc syringe then extruded through a tube die into a 4% by weight aqueous solution of tribasic potassium phosphate (pH=11). The tube formed was left in the potassium phosphate solution overnight. The tube was then dialyzed in deionized water. The tubing was then placed into a 4% by weight aqueous solution of $CaCl_2 \cdot 2H_2O$ and left overnight.

EXAMPLE 3

Chitosan gel exposure to encapsulated lysozyme and effect of phosphate.

Two lengths of the tubing made in Example 2 were placed into separate 1 oz jars. One jar contained a piece of calcium-alginate fiber prepared in Example 1 and deionized water. The second jar contained calcium-alginate fiber prepared in Example 1 and a 0.25% phosphate solution. The jars were placed into a water bath at 37° C. The calcium-alginate fiber in the jar containing phosphate solution disintegrated within 12 hours while the calcium-alginate fiber in water remained intact. The chitosan tube present in the jar with the disintegrated calcium-alginate fiber began to weaken, crumble and fall apart within 48 hours. The chitosan tube present in the container with the intact calcium alginate fiber maintained good mechanical integrity for 1 week after which the study was terminated.

What is claimed is:

1. A composition suitable for use in the fabrication of medical devices comprising:

a) a matrix polymer which is essentially insoluble in body fluids and;

b) a disintegration agent which acts to decompose said matrix polymer when contacted therewith, said disintegration agent being contained within and chemically isolated from said matrix polymer by encapsulation in an ionically crosslinked second polymer or by presence in an interpolyelectrolyte complex, wherein said disintegration agent is selected from the group consisting of enzymes, acids, bases and electrolytes, and wherein said interpolyelectrolyte complex is a complex of the disintegration agent with an oppositely charged partner.

2. The composition of claim 1 wherein said disintegration agent is chemically isolated from said matrix polymer by encapsulation in an ionically crosslinked second polymer.

3. The composition of claim 2 wherein said disintegration agent is selected from the group consisting of enzymes, acids, bases and electrolytes.

4. The composition of claim 2 wherein said matrix polymer is crosslinked ionic polymer.

5. The composition of claim 4 wherein said matrix polymer comprises an ionically crosslinked anionic polymer selected from the group consisting of polyacrylic acid, polymethacrylic acid, alginic acid, pectinic acid, carboxymethyl cellulose, hyaluronic acid, heparin, carboxymethyl starch, carboxymethyl dextran, heparin sulfate, and chondroitin sulfate, and salts thereof.

6. The composition of claim 5 wherein said matrix polymer is an ionically crosslinked anionic polymer comprising at least one polymer selected from the group consisting of alginic acid, pectinic acid, carboxymethyl cellulose, hyaluronic acid, and salts thereof.

7. The composition of claim 4 wherein said matrix polymer is a polysaccharide.

8. The composition of claim 4 wherein said matrix polymer comprises an ionically crosslinked cationic polymer selected from the group consisting of chitosan, cationic guar, cationic starch and polyethylene amine.

9. The composition of claim 2 wherein said ionically crosslinked second polymer contains carboxylic, sulfate or amine functionality.

10. The composition of claim 9 wherein said ionically crosslinked second polymer is selected from the group consisting of alginic acid, pectinic acid, carboxymethyl cellulose, chitosan and salts thereof.

11. The composition of claim 2 wherein said ionically crosslinked second polymer is selected from the group consisting of calcium alginate and calcium pectinate.

12. The composition of claim 2 wherein said matrix polymer is selected from the group consisting of chitosan, alginic acid, pectinic acid, carboxymethyl cellulose, hyaluronic acid and their salts.

13. The composition of claim 2 wherein said disintegration agent is an enzyme.

14. The composition of claim 1 wherein said disintegration agent is chemically isolated from said matrix polymer by presence in an interpolyelectrolyte complex, wherein said interpolyelectrolyte complex is a complex of the disintegration agent with an oppositely charged partner.

15. A shaped medical device having the composition of claim 2.

16. A shaped medical device having the composition of claim 14.

17. A process for the in vivo decomposition of the device of claim 15 comprising contacting said device in vivo with a releasing agent capable of displacing crosslinking ions present in said ionically crosslinked second polymer.

18. A process for the in vivo decomposition of the device of claim 16 comprising contacting said device in vivo with a releasing agent capable of displacing crosslinking ions present in said interpolyelectrolyte complex.

19. The process of claim 17 wherein said disintegration agent is selected from the group consisting of enzymes, acids, bases and electrolytes.

20. The process of claim 17 wherein said releasing agent is selected from the group consisting of ethylene diamine tetraacetic acid, ethylene diamine tetraacetate, citrate, organic phosphates, inorganic phosphates, trisodium carboxymethyloxysuccinate, nitrilotriacetic acid, maleic acid, oxalate, polyacrylic acid, and sodium, potassium, calcium and magnesium ions.

21. The process of claim 17 wherein said matrix polymer is a crosslinked ionic polymer.

22. The process of claim 21 wherein said matrix polymer is a polysaccharide.

23. The process of claim 17 wherein said ionically crosslinked second polymer is selected from the group consisting of alginic acid, pectinic acid, carboxymethyl cellulose, chitosan and salts thereof.

24. The process of claim 17 wherein said ionically crosslinked second polymer is selected from the group consisting of calcium alginate and calcium pectinate.

25. The process of claim 24 wherein said releasing agent is a source of phosphate ions.

26. The process of claim 17 wherein said matrix polymer is selected from the group consisting of chitosan, alginic acid, pectinic acid, carboxymethyl cellulose, hyaluronic acid and their salts.

27. The process of claim 18 wherein said releasing agent is an electrolyte capable of displacing ions present in said interpolyelectrolyte complex.

28. The composition of claim 14 wherein the disintegration agent comprises an enzyme with an overall cationic charge.

29. The composition of claim 14 wherein said matrix polymer comprises an ionically crosslinked ionic polymer.

30. The composition of claim 29 wherein said matrix polymer is an ionically crosslinked anionic polymer comprising at least one polymer selected from the group consisting of alginic acid, pectinic acid, carboxymethyl cellulose, hyaluronic acid, and salts thereof.

31. The composition of claim 29 wherein said matrix polymer is an ionically crosslinked polysaccharide.

32. The composition of claim 29 wherein the matrix polymer is an ionically crosslinked cationic polymer selected from the group consisting of chitosan, cationic guar, cationic starch and polyethylene amine.

33. The medical device of claim 15 wherein the medical device is a shaped medical device selected from the group consisting of stents, catheter components, cannula components, plugs and constrictors.

34. The medical device of claim 16 wherein the medical device is a shaped medical device selected from the group consisting of stents, catheter components, cannula components, plugs and constrictors.

35. The process of claim 18 wherein the releasing agent is a source of phosphate ions.

36. The process of claim 17 wherein the releasing agent is contacted with the medical device in vivo by means of introduction through the diet, parenteral feeding, insertion of a catheter which injects the agent within the device, or through an enema.

37. The process of claim 18 wherein the releasing agent is contacted with the medical device in vivo by means of introduction through the diet, parenteral feeding, insertion of a catheter which injects the agent within the device, or through an enema.

* * * * *